United States Patent [19]

Doyle

[11] Patent Number: 4,473,295
[45] Date of Patent: Sep. 25, 1984

[54] PARABOLIC FOCUSING APPARATUS FOR OPTICAL SPECTROSCOPY

[75] Inventor: Walter M. Doyle, Laguna Beach, Calif.

[73] Assignee: Laser Precision Corporation, Utica, N.Y.

[21] Appl. No.: 298,067

[22] Filed: Aug. 31, 1981

[51] Int. Cl.³ .............................................. G01N 21/01
[52] U.S. Cl. ..................................... 356/244; 356/73
[58] Field of Search ............... 356/244, 445, 446, 300, 356/346, 245, 246, 73; 250/347, 353; 350/294

[56] References Cited

U.S. PATENT DOCUMENTS

| | | | |
|---|---|---|---|
| 3,240,111 | 3/1966 | Sherman et al. | 356/300 |
| 3,491,366 | 1/1970 | Harrick | 356/300 |
| 3,958,882 | 5/1976 | Gast | 356/73 |
| 4,109,149 | 8/1978 | Abel et al. | 250/347 |

OTHER PUBLICATIONS

Gast et al., "An Amplitude Fourier Spectrometer for Infrared Solid State Spectroscopy", Optics Communications, vol. 8, No. 1, pp. 26-30, May 1973.

Primary Examiner—Vincent P. McGraw
Attorney, Agent, or Firm—Thomas J. Plante

[57] ABSTRACT

An accessory for optical spectroscopy is disclosed which combines a matched pair of off-axis paraboloid reflecting surfaces having their focal points at a common location on the reflecting surface of a sample. The entering and exiting beams are collimated. Preferably the paraboloid reflecting surfaces have co-linear, anti-parallel axes, and are part of a unitary structure which is rotatable around the collimated optical beam axis to vary the angle of incidence on the sample without altering the optical alignment, thereby allowing the specular reflectance component to be included or excluded, at will.

23 Claims, 13 Drawing Figures

PARABOLIC FOCUSING APPARATUS FOR OPTICAL SPECTROSCOPY

BACKGROUND OF THE INVENTION

This invention relates to optical spectroscopy, and particularly to focusing accessories for use in directing the radiation to, and receiving the radiation from, a sample under analysis.

Such accessories may conveniently be considered in two general categories. One category includes reflectance accessories in which the radiation leaving the sample holder is travelling in a different direction from the radiation reaching the sample holder because of its reflectance by the sample. The other category includes accessories in which the radiation leaving the sample holder is travelling in essentially the same direction as the radiation reaching the sample holder. In Doyle application Ser. No. 291,402, filed Aug. 10, 1981, and having the same assignee as this application, an accessory of the latter category is disclosed.

The present invention relates to accessories of the former category, and particularly to apparatus which is useful in analyzing samples both in the diffuse reflectance mode and in the specular reflectance mode. Although reflectance accessories of the type disclosed herein can be used with a wide variety of spectrometers, they are particularly suited for use with Fourier Transform infrared (FTIR) instruments and make use of the fact that the sample region beams in these instruments can be made available in a collimated form with a circular cross section.

Optical spectrometers normally function by transmitting a beam of radiation through a sample of a material under study. The wavelengths of the radiation beam are encoded in various ways so as to make possible the recording of a transmission spectrum of the material (ie: optical transmission vs wavelength). In all of the earlier instruments, and a majority of present instruments, wavelength encoding has been accomplished by using a diffraction grating or a prism to spectrally disperse the radiation. The radiation is then brought to a focus, allowing a slit to be used to select a narrow region of the spectrum for transmission through the sample, which is placed in the "sample" region immediately after the slit. The divergent nature of the radiation beam emerging from the slit establishes the constraints on sample size and shape as well as the design of sampling accessories.

Over the years, a large number of accessories have been designed for use with dispersive spectrometers. These allow the normal transmission geometry to be converted for use in such measurements as microsampling, attenuated total reflectance, specular reflectance and diffuse reflectance. In each case, the accessory has had to start with a diverging beam, refocus it at the surface of a sample, collect the transmitted or reflected radiation, and reconfigure it to appear as if it were still diverging from the original slit position. These multiple requirements have generally led to rather complex designs entailing typically five or six reflections, critical positioning in the sample compartment, and critical adjustment of the various mirror positions. Sheets 12-15 of the loose-leaf, undated catalogue of Harrick Scientific Corporation illustrate some of the typical designs.

Considerable difficulty with such accessory designs results from the need to start with a beam focused at a slit and end with a beam which appears to be diverging from the same slit position. Alteration of this basic geometry would require corresponding changes in the detector optics to enable the radiation to be collected and imaged on the optical detector.

Over the past ten years or so, Fourier Transform Infrared (FTIR) spectrometers have come into common use. In these instruments, wavelength encoding is accomplished by a Michelson interferometer rather than a dispersive device. One result is the elimination of the usual slit. In fact, the beam emerging from the interferometer is most typically collimated (to within a degree or two) and has a circular cross section. Despite this, FTIR manufacturers equip their instruments with auxiliary optics to bring the beam to a focus in the sample region. This is done to minimize required sample size and to make the instruments compatible with the large number of accessories designed for dispersive instruments. The sample region geometry of the Nicolet MX-1 spectrometer is illustrated in the Nicolet publication "Optical Layouts and Specifications of Nicolet FTIR spectrometers", revised March 1980.

Recently there has been considerable interest in diffuse reflectance infrared Fourier transform (DRIFT) spectroscopy, and one FTIR manufacturer (Digilab) is selling an accessory specifically designed for this work, as illustrated in the paper by K. Krishnan, et. al in American Laboratory, March 1980, page 104. This device is designed for use with a focused beam and uses a total of five mirrors.

Fuller and Griffiths, as explained in an article in American Laboratory, October 1978, Page 69, have developed a diffuse reflectance accessory which maximizes the total signal reaching the detector, in part by dispensing with the normal sample region focusing optics. However, this design requires remounting the IR detector in a fixed position relative to the accessory and, therefore, sacrifices the convenience which results when an accessory can be simply dropped into the sample compartment without upsetting the FTIR instrument's detector alignment.

The present invention is intended to provide a reflectance apparatus, for use in spectroscopic instruments, which will have the following advantages over previous apparatus:

(1) Improved adaptability, and accurate adjustability, to permit use either for analysis of diffuse reflectance, or for analysis of specular reflectance;

(2) Capability of being "dropped into" an existing spectrometric instrument without interfering with, or requiring repositioning of, the optical beam, the mirrors, or the detector, of the basic instrument;

(3) Capability of locating the sample in a noninterfering position, while at the same time providing a small focal point size ahd high collection efficiency for micro-reflectance experiments;

(4) Quality of aberration compensation because of preservation of the angular beam divergence, which is a significant advantage when used with specular samples;

(5) Avoidance of any requirement for X, Y or Z translational adjustments of the accessory apparatus, and (6) Using a minimum number of optical elements.

SUMMARY OF THE INVENTION

The present invention provides an accessory for optical spectroscopy which combines a matched pair of off-axis paraboloid reflecting surfaces having their focal points at a common location on the reflecting surface of a sample. The entering and exiting beams are collimated.

Preferably the paraboloid reflecting surfaces have colinear, anti-parallel axes, and are part of a unitary structure which is rotatable around the collimated optical beam axis to vary the angle of incidence on the sample without altering the optical alignment, thereby allowing the specular reflectance component to be included or excluded, at will.

DETAILED DESCRIPTION OF SPECIFIC EMBODIMENTS

Figure 1:
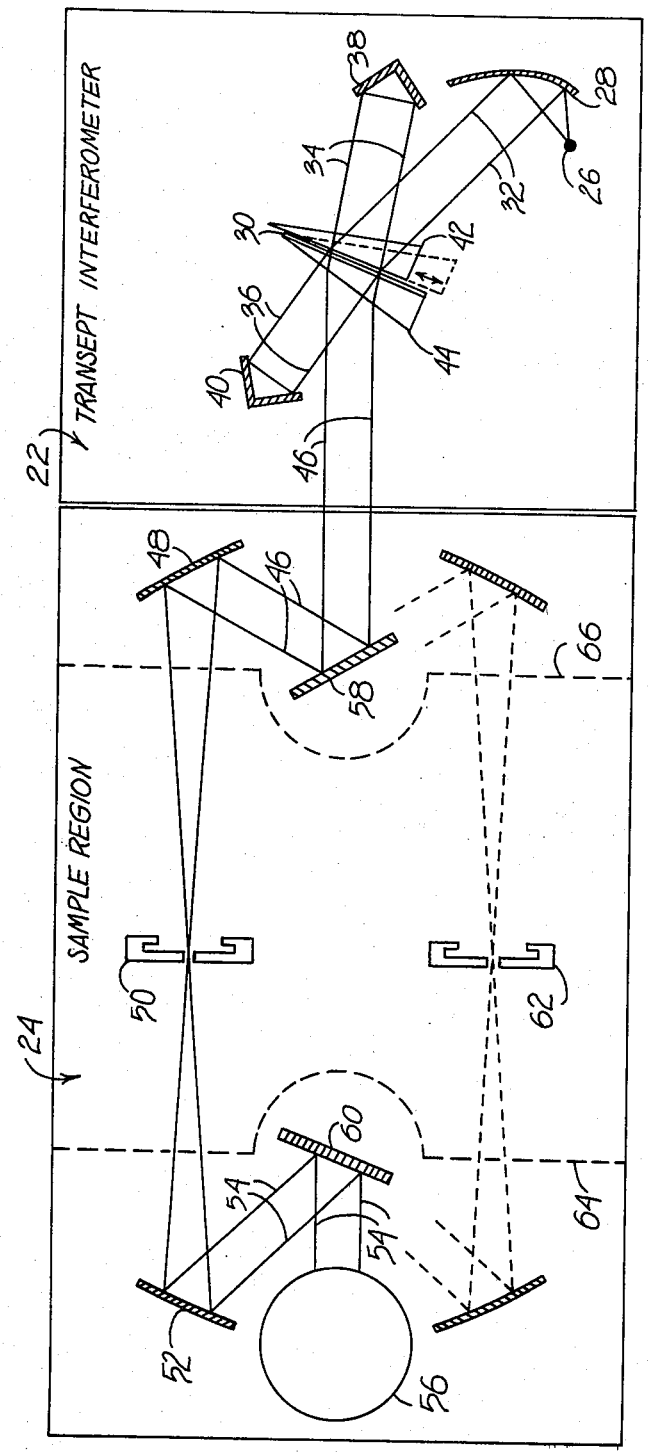
FIG. 1 is a schematic showing the optical components of a spectrometer being marketed by the assignee of the present application, the figure showing the basic unit comprising a "transept interferometer" portion and a "sample region" portion.

FIG. 1 shows an appropriate environment for the use of an optical accessory incorporating the concepts of the present invention. However, the use of the present invention is not limited to the type of spectrometer shown in FIG. 1.

The spectrometer shown is based on several inventions having the same assignee as the present application, including the inventions disclosed in Doyle U.S. Pat. No. 4,165,938, issued Aug. 28, 1979; U.S. Pat. No. 4,190,366, issued Feb. 27, 1980; and U.S. Pat. No. 4,265,540, issued May 5, 1981.

The prior patents referred to were concerned primarily with the interferometer portion of the spectrometer, which is labeled "Transept Interferometer" in FIG. 1 and is generally indicated by numeral 22. The present application is primarily concerned with the sample illuminating portion of the spectrometer, which is labeled "Sample Region" in FIG. 1 and is generally indicated by numeral 24.

The interferometer portion 22 includes a radiation source 26; a paraboloid reflecting mirror 28; a beamsplitter coating 30 which partially reflects and partially transmits the radiation beam 32 coming from mirror 28; two interferometer "arms" provided by the reflected radiation beam 34 and the transmitted radiation beam 36; two stationary retro-reflectors 38 and 40 which constitute the "ends" of the respective interferometer arms; a movable wedge-shaped prism 42 which moves across the path of beam 34 to cause refractive scanning; and a compensating stationary wedge-shaped prism 44 which carries the beamsplitter coating 30.

The operation of the interferometer portion has been fully described in the prior patents referred to above, which are incorporated herein by reference for the purpose of providing a more detailed disclosure of the interferometer portion of the spectrometer.

Attention is called to the fact that the radiation beams 32, 34 and 36 in the interferometer portion are all in collimated form. And the output beam 46 from the interferometer portion is also in collimated form.

In the basic version of the spectrometer shown in FIG. 1, the sample region contains an off-axis paraboloid reflector 48 which receives the collimated beam 46 and focuses it at the sample supported in a sample holder 50, and an off-axis paraboloid reflector 52 which receives the diverging beam after it passes through the sample and provides a collimated output beam 54 transmitted to a detector 56. Two flat mirrors 58 and 60 may be provided at opposite sides of the sample region to direct the incoming beam 46 to paraboloid 48 and to direct the output beam 54 from paraboloid 52 to detector 56.

As shown by the dashed lines illustrating optical rays in the lower part of the sample region, the flat mirrors 58 and 60 may be rotated to different positions to direct a focusing beam to, and receive a diverging beam from, a second sample holder 62. This position-switching of mirrors 58 and 60 provides a dual beam capability for interleaved background measurements. In such usage, the output beam of the interferometer is switched alternately between two similar paths, one serving as a sample path and the other as the background path. In this case, a single scan output display corresponds to the ratio between one sample spectrum and one background spectrum. For a multiple scan measurement, the alternate sample and background spectra are independently averaged, and an up-dated ratio is computed after each pair of scans.

When an accessory, such as the reflecting accessory disclosed in this application, is inserted into the spectrometer, the collimated beam portion of the sample region having the flat mirrors (note description below) can be reserved for accessory inter-facing, while the other beam remains in the normal focused configuration.

The present invention is particularly useful as an accessory which can be inserted in the sample region 24 with little or no change in the basic spectrometer as shown in FIG. 1. It is insertable between the input beam 46 received by the sample region from the interferometer portion 22 and the output beam 54 directed to the detector 56. Since the dotted lines 64 and 66 in FIG. 1 outline the sample chamber, the accessory may be designed to fit in the area between those. However, the present invention can be incorporated into spectrometers in many other arrangements.

The radiation beam entering the accessory, and the radiation beam leaving the accessory, need to be collimated, for reasons which will become apparent during the following description. Accordingly, in order to insert the accessory into the existing sample chamber of FIG. 1, it is necessary to replace the paraboloid reflectors 48 and 52 with flat reflectors.

Figure 2:
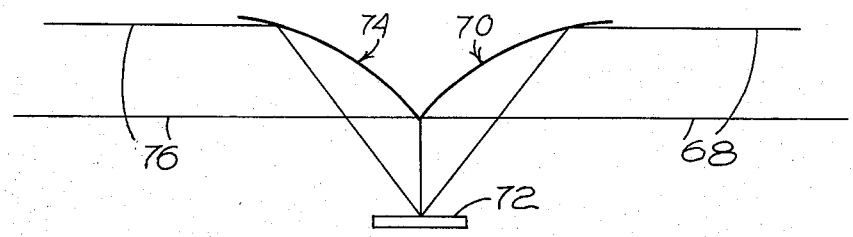
FIG. 2 is a side elevation, partly schematic, of a reflectance accessory, of the type disclosed in this application, installed in the sample region of the spectrometer of FIG. 1.

As shown in FIG. 2, a collimated radiation beam 68, which is in effect a continuation of collimated beam 46 from the interferometer, enters the right side of the sample chamber and is reflected by a first off-axis paraboloid reflector 70 in such a way as to focus at the point where it is reflected by the surface of a sample contained in (or on) a sample holder 72. The diverging beam reflected from the sample strikes a second off-axis paraboloid reflector 74, which also has its focal point at the surface of the sample. The second paraboloid 74 provides a collimated reflected beam 76 which is transmitted to the detector.

Figure 9:
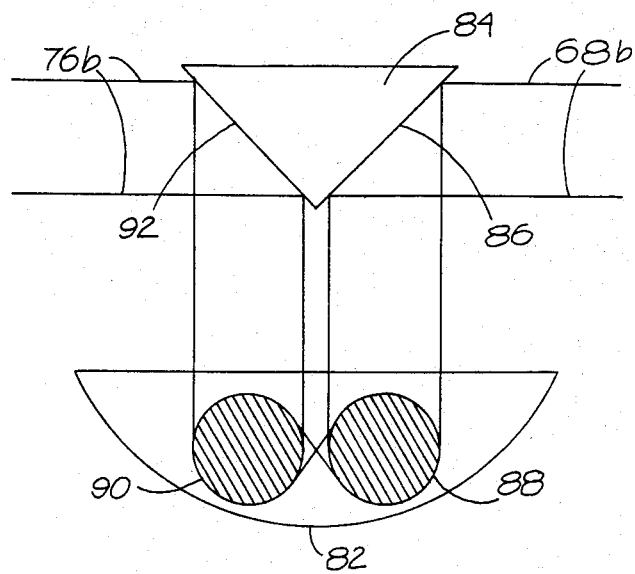
FIGS. 9 and 10 show still another modified version of the accessory in which the entering and exiting optical beams are reflected from different surfaces of the same parabolic reflector, FIG. 9 being a horizontal projection, and FIG. 10 a vertical projection, of the structure.
Figure 10:
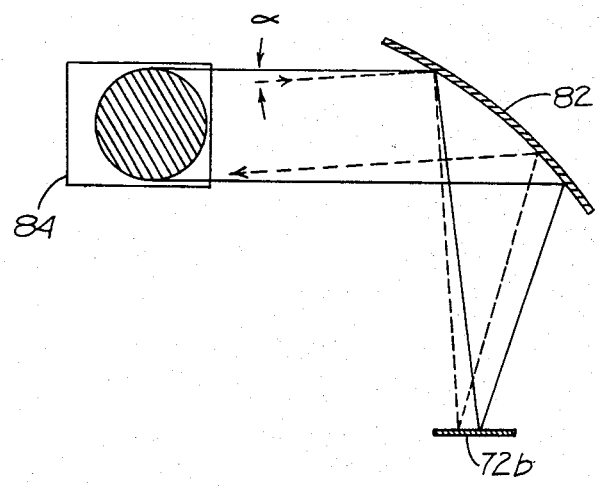

In its most general form, the present invention is a reflectance apparatus having two parabolic mirrors positioned so that their focal points are superimposed at the sample position, and having collimated entering and exiting beams. When this condition is met, collimated radiation which strikes one of the mirrors parallel to its axis of rotation will reach the common focus, and any portion of the reflected radiation which reaches the second mirror will be recollimated by it and directed on a path toward the detector. This combination of characteristics makes it possible to provide a reflectance accessory having only two focusing elements, or surfaces, which are the two paraboloid reflectors 70 and 74, or, as shown in FIGS. 9 and 10, two spaced reflecting surfaces on the same paraboloid. Thus, an accessory is obtained which minimizes the number of included optical elements, and which provides an extremely simple, rugged and reliable construction.

The preferred version is that shown in FIGS. 2–6 and 11–13. In those figures, the two paraboloids 70 and 74 are the only optical elements which the reflectance accessory adds to the spectrometer when it is dropped into place in the sample chamber. Preferably, for many reasons, the two paraboloids are rigidly secured together and are rotatably mounted in a supporting structure which maintains their alignment while permitting them to be rotated as a unit around the co-linear axes of the collimated optical beams.

In any of the embodiments shown, the accessory is a rigid, unitary structure which is added to, or removed from, the sample chamber as a single member.

Because the paraboloids 70 and 74 have parallel axes, the recollimated exiting radiation reflected by paraboloid 74 is parallel to the entering collimated radiation received by paraboloid 70. And because the axes of the two paraboloids are colinear, the angle of reflectance on the sample may be readily adjusted. The benefits of these features will be discussed at greater length below.

Figure 7:
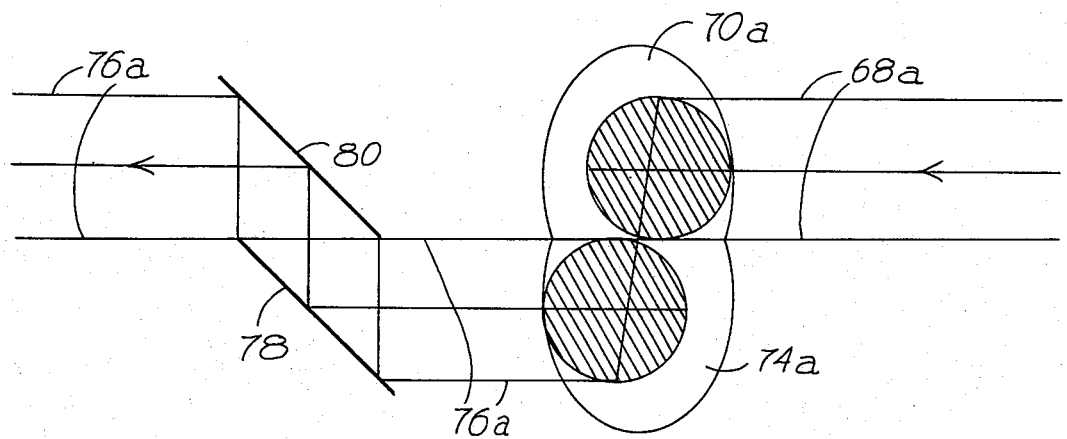
FIGS. 7 and 8 show a modified version of the accessory in which two paraboloid reflectors are mounted side-by-side, instead of back-to-back, FIG. 7 being a horizontal projection, and FIG. 8 a vertical projection, of the structure.
Figure 8:
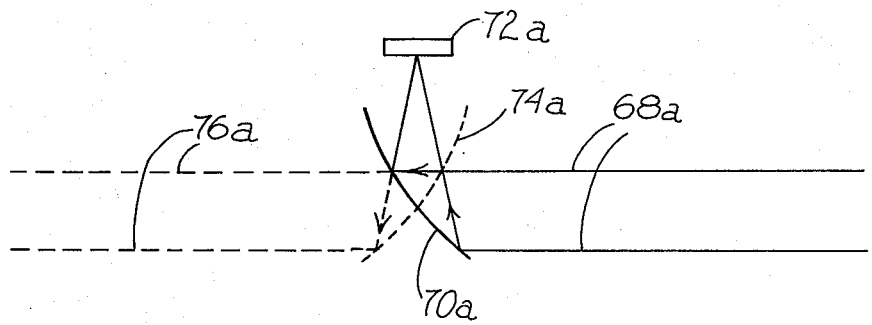

FIGS. 7 and 8 show a modified version of the accessory in which two paraboloid reflectors 70a and 74a are mounted side-by-side (instead of a co-linearly). The collimated entering beam 68a is reflected by paraboloid 70a onto a sample 72a (see FIG. 8), which is shown located above the level of the entering and exiting beams.

After being focused on, and reflected by, the sample 72a, the radiation strikes paraboloid 74a, and is recollimated, as shown by exiting beam 76a. Since the emergent beam 76a has been laterally displaced from the incident beam 68a, a pair of plane mirror 78 and 80 are required to make the incident and emergent beams co-linear. In other words, in FIGS. 7 and 8, the two paraboloids have been placed side-by-side, but they still have a common focal point, and their axes are still anti-parallel (parallel but oppositely directed).

A third embodiment is shown in FIGS. 9 and 10. In this version, a single paraboloid 82 is used for both focusing and collecting the radiation. The focusing and collecting portions of the mirror are thus automatically aligned to share the same focus. Since the reflected beam is antiparallel to the incident beam, it is necessary to use a pair of flat mirrors, or a 90° rooftop mirror 84, to make the two beams (incident beam 68b and emergent beam 76b) co-linear. The entering beam 68b, after being reflected by surface 86 of rooftop mirror 84, strikes the surface area 88 of the paraboloid, and is reflected toward the sample 72b (see FIG. 10). The focused beam is reflected from the sample to strike the surface area 90 of the paraboloid, which recollimates it, and directs it toward surface 92 of rooftop mirror 84.

The design of FIGS. 9 and 10 does not possess the quality of preserving the beam divergence angle, which will be discussed below. It therefore is not desirable for use with very short focal length paraboloids, i.e., those having a substantial difference in focal length between the two edges of the beam. However, it does have one useful characteristic not shared by the first two designs in that it tends to act as a retroreflector. As illustrated by the dashed lines in FIG. 10, a ray which strikes the mirror at angle $\alpha$ will leave the paraboloid at an angle approximately equal to $\alpha$ (except as modified by the variations in focal length) rather than $-\alpha$ as in the other designs. The significance of this feature is that, at least for small angles, the performance of the accessory will be independent of angular position in the sample region. In the other designs, any angular misalignment would lead to a deviation of the collimated beam by an angle equal to twice the alignment error.

As previously stated, the clearly preferred version of the invention is that shown in FIGS. 2–6 and 11–13, in which the collimated beam striking the first paraboloid is colinear with the collimated beam leaving the second paraboloid. This provides several significant benefits, some of which are shared with other embodiments, and some of which are not.

The structure of the preferred version is particularly simple and efficient because it incorporates only the two paraboloids, mounted in a suitable holder. This aspect will be discussed more fully in the description below of the detailed structure shown in FIGS. 11–13.

Another benefit of the preferred version, which it shares with the embodiment shown in FIGS. 7 and 8, is the essentially aberration-free quality of the reflected radiation. This quality is important when the instrument is being used with a specular target, such as a coated metal surface, but not particularly important when the instrument is being used with a diffuse target, such as powder.

Figure 6:
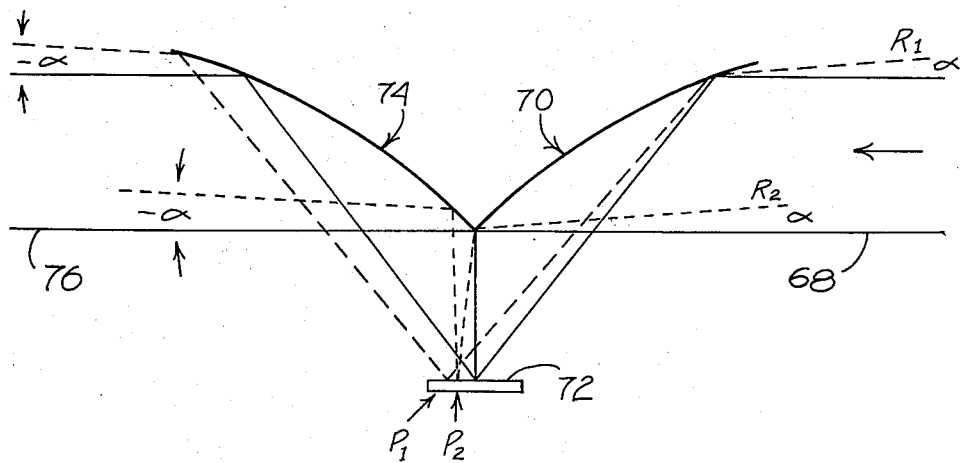
FIG. 6 is a schematic similar to FIG. 2 showing how aberration compensation is provided by the accessory.

FIG. 6 illustrates the aberration compensation feature, which results from the fact that an optical ray which initially strikes the upper part of the first paraboloid mirror 70 will eventually strike the upper part of the second paraboloid mirror 74. This is an important feature in that it tends to prevent any divergence of the input beam from being increased by the accessory. Referring to the figure, assume that the beam emerging from the interferometer has a divergence angle of $\alpha$ on either side of its axis. As is evident from the figure, the lower part of each paraboloid has a different effective focal length from the upper part. Thus rays $R_1$ and $R_2$ will strike the target at different points, $P_1$ and $P_2$, even though they initially make the same angle with the beam axis. With the mirror geometry shown and a specular target, the radiation reflected from $P_1$ will be collected by a segment of the mirror having about the same focal length as the segment used to image it on the sample. It will thus leave the second mirror with an angle approximately equal to its angle of incidence, although with the opposite sign. This is also true of a ray striking $P_2$. Thus the accessory does not increase the divergence of the beam.

When a diffuse sample is illuminated, the direction of the reflected radiation will not be strongly correlated with the input direction. Thus some of the radiation from $P_1$ will strike the lower region of the second mirror and will thus emerge with a divergence angle greater than $\alpha$. The beam divergence will thus be increased.

Still another benefit of the preferred version, which is not possessed by the other embodiments, is its feature of easy, simultaneous position-adjustment of the two parabolic mirrors to vary the portion of specular reflection which is included in the emergent beam.

As shown in FIG. 2, the axes of the paraboloids 70 and 74 are colinear, and the entering and exiting collimated beams 68 and 76 are also colinear. Mounting the two paraboloids in a rigid structure, or assembly, which can be position-adjusted by rotating it around the co-linear axes of the two collimated optical beams, allows the angle of incidence of the focused beam on the sample to be varied without altering the commonality of the focal points of the two paraboloids.

Figure 3:
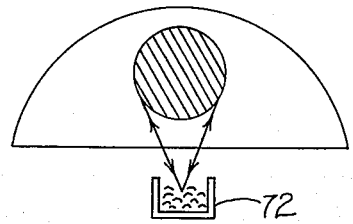
FIG. 3 is a view taken at right angles to FIG. 2, showing the collimated beam (either entering or exiting the accessory) in cross section, in which the angle of incidence is adjusted to provide total reflectance, and in which a powdered sample is held in a container.

As shown in FIG. 3, the position-adjustable, two paraboloid assembly may be positioned so that the beam is directed vertically downward, providing a minimum angle of incidence, which may be desired either with highly diffuse powdered samples, or with specular samples, but not with portly diffuse, partly specular samples. In other words, a substantially perpendicular light beam on the sample is satisfactory if the sample surface is either purely specular or purely diffuse.

Figure 4:
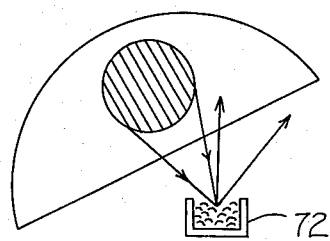
FIG. 4 is similar to FIG. 3, except that the angle of incidence is adjusted to eliminate the specular component and to collect diffuse reflectance only.

As shown in FIG. 4, the position-adjustable, two paraboloid assembly has been rotated approximately 20° around the colinear axes of the entering and exiting collimated beams 68 and 76, in order to eliminate the specular component and collect only the diffuse reflection at the second paraboloid 74. The arrows show that the specular reflection from the sample surface will not reach that portion of the second paraboloid 74 which reflects the collimated beam to the detector. The relative positions of the collimated beam 68 and the sample 72 in FIG. 4 have been changed from their relative positions in FIG. 3 by moving the sample 72 along a suitable guiding track perpendicular to beam 68; the position of the beam has not changed although it appears slightly further left in FIG. 4. During rotation of the unitary two-paraboloid assembly, its focal point moves to remain on the colinear focal axes of the two paraboloids.

The samples shown in both FIGS. 3 and 4 are powdered samples (in cup-shaped holder 72), which samples provide primarily diffuse reflection. In the position of FIG. 3, the specular reflection component is included in the emergent radiation, whereas in the position of FIG. 4 the specular reflection component is excluded from the emergent radiation. It is a significant advantage that the sample, although moved laterally, level position, while the angular position adjustment is made by rotating the unitary optical assembly. The sample does not need to be tilted to change the angle of incidence.

Figure 5:
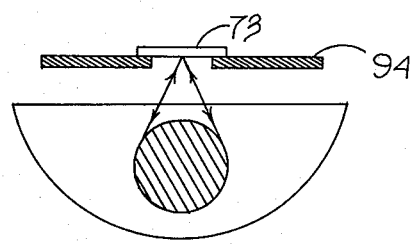
FIG. 5 is similar to FIG. 3, except that a specular sample is supported on a flat surface above the optical beam, and the position of the reflecting unit is appropriately adjusted.

FIG. 5 shows the unitary two-paraboloid structure rotated 180° around the colinear axes of the entering and exiting collimated beams 68 and 76, so the focal point on the sample 73 is directly above the collimated incident and emergent beams. This arrangement is used for solid samples which provide primarily specular reflection. Such a sample can have its reflecting surface automatically positioned in the focal plane by lying on a sample carrier 94, which is supported on the top of the accessory structure when the instrument is in the position of FIG. 5.

Figure 11:
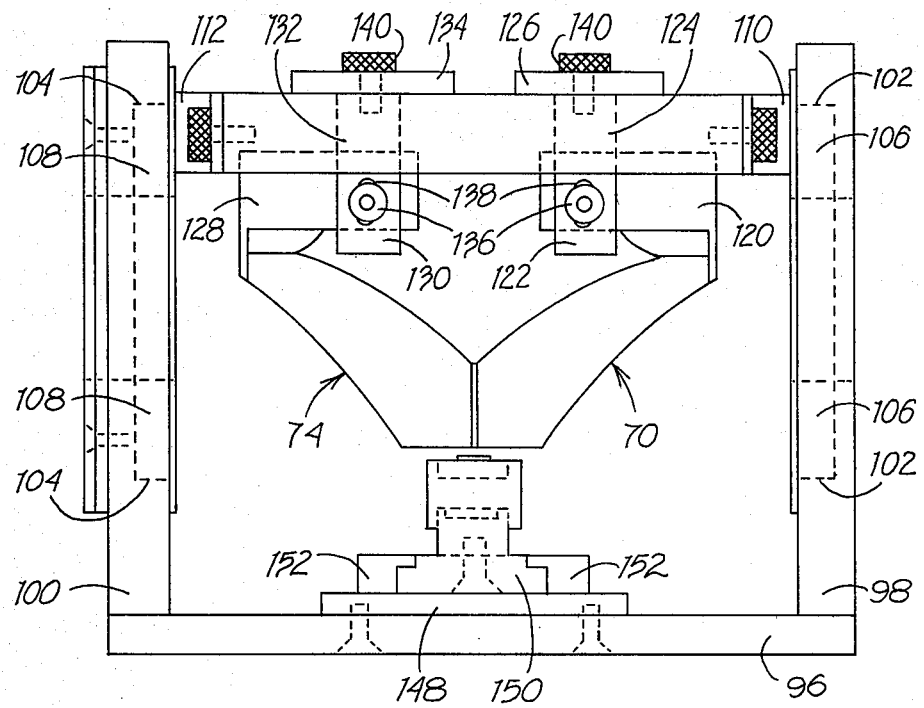
FIG. 11 is a side elevation, partly in cross section, of a complete accessory structure incorporating the concepts of the preferred embodiment, the reflecting structure being shown in the diffuse reflectance mode.
Figure 12:
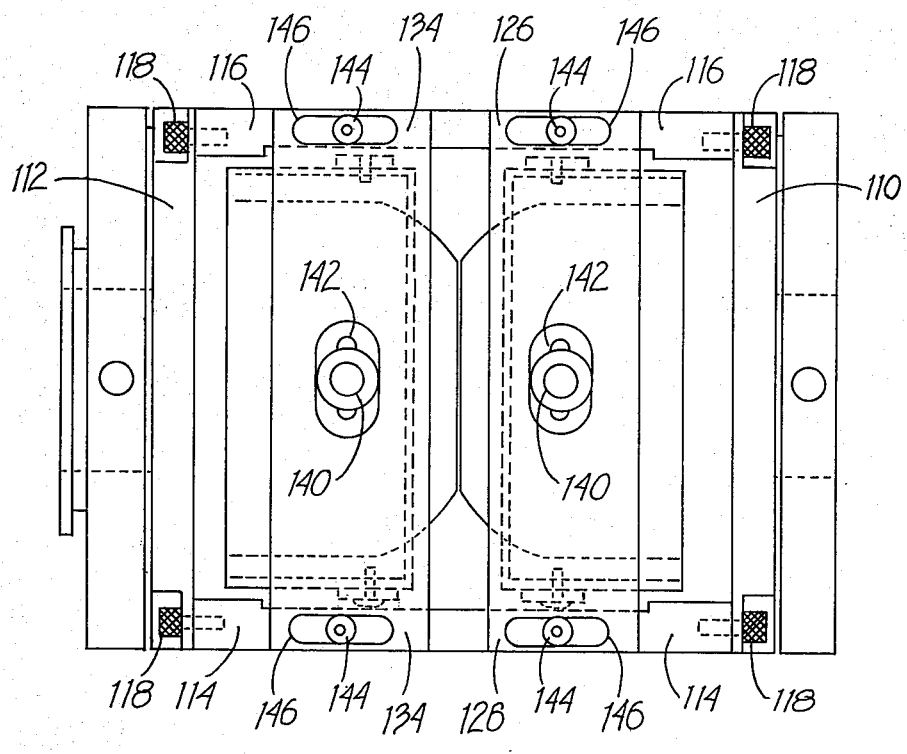
FIG. 12 is a plan view of the accessory structure of FIG. 11.
Figure 13:
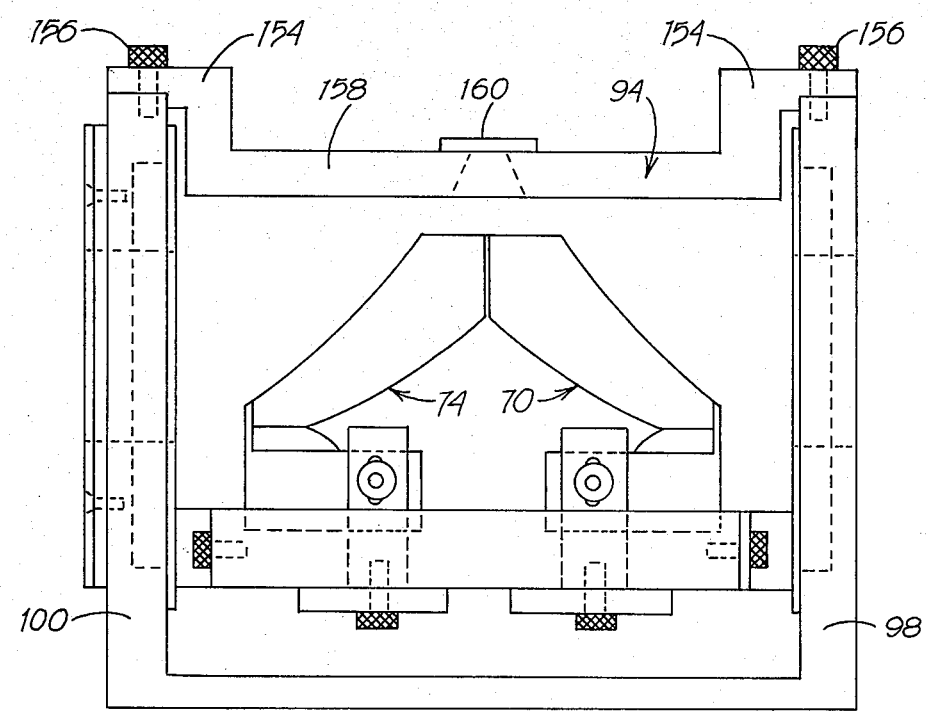
FIG. 13 is another side elevation of the same accessory structure as FIG. 11, except that the reflecting structure is shown in the specular reflectance mode.

FIGS. 11–13 show the detailed construction of a unitary reflectance accessory, suitable for insertion in the sample region of the spectrometer. The frame of the accessory comprises a horizontal platform 96 and two vertical support members 98 and 100. The two vertical support members have aligned circular cutouts 102 and 104, respectively, adapted to receive rotatable end portions of a unitary supporting structure which carries the two paraboloids.

The unitary structure which carries the paraboloids comprises two annular rotation plates 106 and 108 which fit into the respective circular cutouts 102 and 104, the plate 106 being on the radiation entering end, and the plate 108 being on the radiation exiting end, of the accessory. At the top of the structure, as seen in FIGS. 11 and 12, the two rotation plates 106 and 108 are rigidly interconected by an open rectangular frame comprising two laterally extending end pieces 110 and 112, and two longitudinally extending side pieces 114 and 116 (see FIG. 12). The end pieces and side pieces of the frame are secured together by threaded fastening members 118; and the frame is secured to the rotation plates by suitable fastening means (not shown).

Each of the two parabolic mirrors is glued to a mount, which is supported at both ends by arms extending downwardly (in FIG. 11) from a bracket, which in turn is secured to a plate extending laterally across the top of the frame. The paraboloid 70 at the entering end is secured to a mount 120, which is supported by two downwardly-extending arms 122 on a bracket 124, the body of which lies against, and is secured to, the underside of a plate 126. Plate 126 lies on top of, and bridges across, the two side pieces 114 and 116 of the rectangular frame. The paraboloid 74 at the exiting end is secured to a mount 128, which is supported by two downwardly-extending arms 130 on a bracket 132, the body of which lies against, and is secured to, the underside of a plate 134. Plate 134 lies on top of, and bridges across, the two side pieces 114 and 116 of the rectangular frame.

Initial adjustment of the position of each paraboloid (70 and 74) is provided by fasteners which extend into oversize holes. Mounts 120 and 128 are secured to bracket arms 122 and 130, respectively, by fasteners 136 extending through oversize holes 138 (FIG. 11). Brackets 124 and 132 are secured to plates 126 and 134, respectively, by fasteners 140 extending through oversize holes 142 (FIG. 12). And plates 126 and 134 are secured to the two side pieces 114 and 116 of the rectangular frame by fasteners 144 extending through oversize holes 146 (FIG. 12).

In order to locate the sample accurately when the accessory is in the position of FIG. 11, a guiding structure 148 is secured to the platform 96, and one or more sample containers are mounted in a carrier 150 which slides in a channel between two retaining flanges 152 secured to the guiding structure 148.

In order to locate the sample accurately when the accessory is in the position of FIG. 13, the sample carrier 94 has its arms 154 attached by lock screws 156 to the tops of the two vertical support members 98 and 100. The sample carrier 94 has a downwardly-suspended central portion 158 on which a specular sample 160 is positioned, the sample carrier having a centrally-located opening to permit radiation to reach the lower surface of sample 160.

The diffuse reflectance (DRIFT) technique can be applied to a wide variety of opaque and/or powdered samples, and has the advantages of relatively easy sample preparation and minimal chemical interaction with the diluting material. A further attractive feature of DRIFT spectroscopy is that, to first order, the band strengths vary as the square root of sample concentration rather than as concentration. This allows useable spectra to be obtained with extremely small amounts of sample material and thus makes the technique especially useful for microsample analysis.

Specular reflectance spectroscopy is most commonly used for the study of absorbing coatings on smooth reflecting surfaces. Typical examples are paint or epoxy coatings on metals or lubricating coatings on magnetic disks.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. For use in a spectrometer adapted to illuminate a sample and comprising (a) an accessory region, (b) means for directing a collimated entering beam into that region, and (c) means for receiving a collimated exting beam from that region; a reflectance accessory for insertion in that region in which the only focusing optical surfaces are:
    a first paraboloid reflecting surface which reflects the entering collimated beam onto a focal point on the surface of the sample; and
    a second paraboloid reflecting surface which has its focal point at the focal point of the first paraboloid, and which receives radiation reflected from the sample and converts it into the collimated exiting beam.

2. The structure of claim 1 in which the two paraboloid reflecting surfaces are provided by two matched paraboloids which have parallel axes.

3. The structure of claim 1 in which the two paraboloid reflecting surfaces are provided by two matched paraboloids which have colinear axes.

4. The structure of claim 1 in which the two paraboloid reflecting surfaces are provided by spaced surfaces on a single paraboloid.

5. The structure of claim 4 which also comprises:
    a first flat reflecting surface for reflecting the entering collimated beam to the first paraboloid reflecting surface; and
    a second flat reflecting surface for reflecting the collimated beam from the second paraboloid reflecting surface to provide the exiting collimated beam.

6. The structure of claim 5 wherein the first and second flat reflecting surfaces are provided by a ninety degree rooftop mirror.

7. The structure of claim 1 or claim 3 in which the axes of the collimated entering and exiting beams are co-linear.

8. The structure of claim 7 which also comprises:
    means for rotating the two paraboloid reflecting surfaces around the optical beam axis in order to vary the angle of incidence of their focused beams on a target surface having a given orientation.

9. The structure of claim 8 which also comprises:
    means for initially adjusting the position of each paraboloid reflecting surface; and
    means for permanently securing the paraboloid reflecting surfaces together in their initially adjusted positions while permitting their rotation as a unit around the optical beam axis.

10. An optical device for directing radiation to cause sample illumination by a spectrometer which includes means for directing a collimated entering radiation beam into the device, means for receiving a collimated exiting radiation beam from the device, and means for providing a sample at a position laterally spaced from the axes of the collimated beams, said device comprising:
    a first paraboloid reflector which reflects the entering collimated beam onto a focal point; and
    a second paraboloid reflector which reflects radiation from a focal point to provide the collimated exiting beam;
    the focal points of the first and second paraboloid reflectors being a common point on a reflecting surface of the sample.

11. The optical device of claim 10 wherein the two paraboloid reflectors are so oriented that the distance between the sample and the point where any given ray of radiation strikes one paraboloid reflector is substantially proportional to the distance between the sample and the point where the same ray of radiation strikes the other paraboloid reflector.

12. The optical device of claim 10 or claim 11 wherein the axes of the first and second paraboloid reflectors are co-linear.

13. The optical device of claim 12 which also comprises:
    means for securing the first and second paraboloid reflectors together permanently in a unitary structure.

14. The optical device of claim 13 which also comprises:
    a first supporting structure which carries the first and second paraboloid reflectors; and a second supporting structure which carries the first supporting structure and which also provides a sample-supporting structure;

the first supporting structure being rotatably mounted on the second supporting structure in such a way that the angle of incidence of reflected radiation on the sample can be varied while automatically maintaining the commonality of the focal points of the first and second paraboloid reflectors.

15. The optical device of claim 14 wherein the entering and exiting collimated beams are colinear, and the axis of rotation of the first supporting structure with respect to the second supporting structure coincides with the colinear axes of the collimated beams.

16. The optical device of claim 15 which also comprises:

means for supporting a diffusely reflecting sample below the axes of the beams; and means for supporting a specularly reflecting sample above the axes of the beams.

17. For use in the sample region of a spectrometer having a collimated radiation beam entering the sample region and a collimated radiation beam exiting the sample region, an optical accessory, of the type in which radiation is reflected from the sample, comprising:

a first paraboloid reflector which reflects the entering collimated beam in such a way as to focus the radiation at the point where it is reflected by the surface of the sample; and a second paraboloid reflector which has a common focal point with the first paraboloid reflector and which receives the radiation after it is reflected by the sample, thereby providing the collimated exiting beam;

the first and second paraboloid reflectors being so oriented that any given ray of radiation strikes both paraboloid reflectors at respective points thereon having substantially the same ratio of focal lengths.

18. The optical accessory of claim 17 wherein the first and second paraboloid reflectors face away from each other in generally opposite directions.

19. The optical accessory of claim 18 in which the first and second paraboloid reflectors have anti-parallel axes such that they face in directions 180° away from one another.

20. A spectrometer comprising:

means for providing a pre-sample collimated radiation beam;

means for receiving a post-sample collimated radiation beam;

the pre-sample and post-sample collimated radiation beams having colinear axes;

first and second paraboloid reflectors mounted back-to-back, with the first paraboloid reflector facing in the direction of the pre-sample radiation beam, and the second paraboloid reflector facing in the direction of the post-sample radiation beam;

the focal points of the first and second paraboloid reflectors coinciding at a reflectance point on the sample, whereby the first paraboloid reflector focuses the pre-sample collimated radiation at the reflectance point on the sample, and the second paraboloid reflector receives radiation reflected from the reflectance point on the sample and converts it into the post-sample collimated radiation.

21. The spectrometer of claim 20 wherein the first and second paraboloid reflectors are held together in a unitary assembly.

22. The spectrometer of claim 21 in which the first and second paraboloid reflectors and the sample are the only elements between the pre-sample and post-sample collimated radiation beams.

23. The spectrometer of claim 21 or 22 which also comprises:

means for mounting the unitary assembly of the first and second paraboloid reflectors in such a way as to permit rotation of the assembly; and means for limiting such rotation to rotation around the colinear axes of the pre-sample and post-sample collimated radiation beams.

* * * * *